US009756852B2

(12) United States Patent
Pate et al.

(10) Patent No.: US 9,756,852 B2
(45) Date of Patent: Sep. 12, 2017

(54) TOPICAL DELIVERY FORMULATION

(71) Applicant: MERIAL INC., Duluth, GA (US)

(72) Inventors: James Pate, Hampton, NJ (US);
Natalya Shub, Allentown, PA (US)

(73) Assignee: MERIAL INC., Duluth, GA (US)

( * ) Notice: Subject to any disclaimer, the term of this patent is extended or adjusted under 35 U.S.C. 154(b) by 60 days.

(21) Appl. No.: 14/600,651

(22) Filed: Jan. 20, 2015

(65) Prior Publication Data

US 2015/0201611 A1 Jul. 23, 2015

Related U.S. Application Data

(60) Provisional application No. 61/929,371, filed on Jan. 20, 2014.

(51) Int. Cl.
| | | |
|---|---|---|
| *A01N 25/34* | (2006.01) | |
| *A01N 25/10* | (2006.01) | |
| *A01N 43/56* | (2006.01) | |
| *A01N 53/00* | (2006.01) | |
| *A61K 9/00* | (2006.01) | |

(52) U.S. Cl.
CPC .............. *A01N 25/10* (2013.01); *A01N 43/56* (2013.01); *A01N 53/00* (2013.01); *A61K 9/0014* (2013.01)

(58) Field of Classification Search
CPC ........ A01N 25/10; A01N 43/56; A01N 53/00; A61K 9/0014
See application file for complete search history.

(56) References Cited

U.S. PATENT DOCUMENTS

| | | |
|---|---|---|
| 3,590,118 A | 6/1971 | Conrady et al. |
| 3,912,667 A * | 10/1975 | Spitzer ................ A61K 8/0208 106/122 |
| 4,374,126 A | 2/1983 | Cardarelli |
| 4,409,206 A | 10/1983 | Stricker |
| 6,010,710 A | 1/2000 | Etchegaray |
| 6,797,724 B2 | 9/2004 | Etchegaray |
| 6,998,131 B2 | 2/2006 | Soll et al. |
| 2010/0178262 A1* | 7/2010 | Kergosien .............. A61K 8/361 424/61 |

FOREIGN PATENT DOCUMENTS

| | | |
|---|---|---|
| EP | 0226240 A1 | 11/1986 |
| WO | 2005/089806 A1 | 9/2005 |
| WO | 2013/014127 A1 | 1/2013 |

OTHER PUBLICATIONS

Volker Buhler, Chapters 1 & 4, entitled "Introduction and product overview" and "Kollicoat SR 30D" in Functional Polymers for the Pharmaceutical Industry, Jan. 2007, pp. 11-12, and 101-154, BASF, Ludwigshafen, Germany.
C. Hauser et al, "Antimicrobial active packaging films based on sorbic acid" in Science and Technology Against Microbial Pathogens: Research, Development and Evaluation, Proceedings of the International Conference on Antimicrobial Research (ICAR2010), Valladolid, Spain, Nov. 3-5, 2010, editor A. Mendez-Vilas Hackensack, NJ: World Scientific, 2011 (ISBN: 978-981-4354-85-1 & ISBN: 981-4354-85-6), pp. 131-134.

* cited by examiner

*Primary Examiner* — Nannette Holloman
(74) *Attorney, Agent, or Firm* — Judy Jarecki-Black; Katrina Bergbauer; Merial Inc.

(57) ABSTRACT

The invention is a pour-on antiparasitic formulation having superior water resistant properties. The pour-on formulation utilizes one or more polymers (water insoluble with or without water soluble) in the range of about 5 to about 40% w/w, one or more solvents in the range of about 50 to about 94% w/w, with or without additive (e.g., isopropanol or ethanol) in the range of about 5 to about 30% w/w, and optionally a plasticizer in the range of about 0.5 to about 25% w/w. The pour-on antiparasitic formulation features limited spreading when applied to animals (cattle, sheep, dogs and the like). The pour-on antiparasitic formulation further partially evaporates, leaving a water resistant polymer matrix that diffuses at least one active ingredient to the animal's skin.

15 Claims, No Drawings

TOPICAL DELIVERY FORMULATION

CROSS-REFERENCE TO RELATED APPLICATIONS

This application claims priority to U.S. Provisional Patent Application No. 61/929,371, filed Jan. 20, 2014.

FIELD OF THE INVENTION

The present disclosure relates generally to topical delivery systems and their manufacture. More specifically, the disclosure relates to topical antiparasitic delivery systems for animals.

BACKGROUND

Animals such as mammals are often susceptible to parasite infestations. These parasites may be ectoparasites, such as insects, and endoparasites such as filariae and worms. Domesticated animals, such as cats and dogs, are often infested with one or more of the following ectoparasites:
- fleas (*Ctenocephalides felis, Ctenocephalides* sp. and the like),
- ticks (*Rhipicephalus* sp., *Ixodes* sp., *Dermacentor* sp., *Amblyomma* sp. and the like),
- mites (*Demodex* sp., *Sarcoptes* sp., *Otodectes* sp. and the like),
- lice (*Trichodectes* sp., *Cheyletielfa* sp., *Linognathus* sp., and the like), and
- flies (*Hematobia* sp., *Musca* sp., *Stomoxys* sp., *Dermatobia* sp., *Cochliomyia* sp., mosquitoes (family Culicidae) and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*) and may also transmit pathogens to humans.

Similarly, ticks are also harmful to the physical and psychological health of the animal or human. However, the most serious problem associated with ticks is that they are the vector of pathogenic agents, which cause diseases in both humans and animals. Major diseases which are caused by ticks include borreliosis (Lyme disease caused by *Borrelia burgdorfen*), babesiosis (or piroplasmosis caused by *Babesia* sp.) and rickettsiosis (also known as Rocky Mountain spotted fever). Ticks also release toxins which cause inflammation or paralysis in the host. Occasionally, these toxins are fatal to the host, such as in the case of the Australian paralysis tick, *Ixodes holocyclus*.

Moreover, mites and lice are particularly difficult to combat since there are very few active substances which act on these parasites and they require frequent treatment. Likewise, farm animals are also susceptible to parasite infestations. For example, cattle are affected by a large number of parasites (e.g., arthropod pests, such as fleas, lice and ticks, and mites). A parasite that is very prevalent among farm animals is the tick genus *Boophilus*. especially those of the species *micropJus* (cattle tick), *decoloratus* and *anulatus*. Ticks, such as *Boophilus microplus*, are particularly difficult to control because they live in the pasture where the farm animals graze. Other important parasites of cattle and sheep are listed below:
- (a) myiases such as *Dermatobia hominis* (known as Berne in Brazil), Hypoderma, and *Cochlyomia hominivorax* (greenbottle); sheep myiases such as *Lucilia sericata*, *Lucilia cuprina* (known as blowfly strike in Australia, New Zealand and South Africa). These are flies whose larva constitutes the animal parasite;
- (b) flies proper, namely those whose adult constitutes the parasite, such as *Haematobia irritans* (i.e., horn fly);
- (c) lice such as *Linognathus vitui* etc.; and
- (d) mites such as *Sarcoptes scabiei* and *Psoroptes ovis*.

The above list is not exhaustive and other ectoparasites are well known in the art to be harmful to animals.

Protection of animals against parasites is essential to insure a healthy and safe environment for animals and their owners. Pour-on and spot-on topical formulations are widely used to deliver treatment against variety of external and internal parasiticids, such as ticks, fleas, flies, mites, worms, etc. These formulations are solutions that are applied onto the back of an animal and allowed to spread or penetrate. To be effective, these formulations need to retain an active in upper layers of skin or drive an active into the skin for systemic absorbtion, and to be able to withstand environmental stress (e.g., rain), to prevent removal of the drug. Depending on the intended use, topical formulations typically consist of a solvent with or without a penetration enhancer (for systemically delivered drugs), or a solvent or co-solvents with addition of spreading agent, and various performance additives for delivery into upper layers of the skin. This is a traditional approach to formulating a topical pour-on or spot-on solution. Currently marketed topical pour-ons for production animals for protection from external parasites do not have good water resistance and need to be re-applied frequently.

For example, the commercial products for control of horn fly on cows provide limited protection lasting from several days to two weeks and require re-application after rain throughout the fly season. This creates unnecessary stress for animals resulting in significant productivity losses and additional labor efforts for farmers.

Current commercially available topical solutions to control horn fly population on cows provide limited duration of protection lasting from several days to about two weeks. Current treatments further require frequent re-application due to a wash-off after exposure to environmental conditions such as rain.

Extension of efficacy to one month or longer will provide continuous protection against the horn fly with less frequent applications. Fewer applications will be less stressful for the animals and less time and labor consuming for the farmers.

There are several problems that contribute to the short duration of the active ingredient(s) in the current pour-on nonsystemic formulations. First, the conventional solvent system (organic solvents) applied topically is expected to spread the active ingredient and retain it on the skin for the duration of the desired treatment period. Second, a complete dose intended to last for the duration of the treatment period is applied at one time. Third, conventional solvent systems are not well formulated to resist some weather challenges. The active ingredient is completely exposed to environmental conditions. The solvent carrying the active ingredient is washed off during rain, rendering it non-efficacious. Fourth, the solvent system may not stay on the animal during the treatment process resulting in a non-efficacious treatment.

Compounds that exhibit a degree of activity against a wide range of ectoparasites including arthopods and insects are known in the art. One such class of compounds is the arylpyrazoles which are referred to, for example, in U.S. Pat. Nos. 5,122,530; 5,246,255; 5,576,429; 5,885,607; 6,010,710; 6,083,519; 6,096,329; 6,685,954; EP 0 234 119 and EP 0 295 117 (U.S. Pat. Nos. 5,232,940; 5,547,974; 5,608,077;

5,714,191; 5,916,618 and 6,372,774); EP 0 352 944 (U.S. Pat. No. 4,963,575); EP 0780378 (U.S. Pat. Nos. 5,817,688; 5,922,885; 5,994,386; 6,124,339; 6,180,798 and 6,395,906); EP 0846686 (U.S. Pat. No. 6,069,157); WO 98/28278, WO 08/05489, U.S. Pat. No. 7,759,381 and U.S. Pat. No. 8,445,519. All of the aforementioned patents and patent publications are herein incorporated by reference.

The arylpyrazoles are known to possess excellent activity against insects, such as fleas and ticks. Fipronil is a specific type of 1-N-arylpyrazole that is particularly effective against fleas and ticks and is the active ingredient in Frontline® and Frontline Plus®. Another arylpyrazole, 1-(2-chloro-6-fluoro-4-trifluoromethylphenyl)-4-dichlorofluoro-methyl-sulfinyl-5-methylpyrazole-3-carbonitrile, has structure and properties similar to fipronil.

Other classes of compounds are also known in the art to be effective parasiticides. Examples include macrocyclic lactones (e.g., avermectins and their derivatives ivermectin, eprinomectin, selamectin, doramectin and abamectin), benzimidazoles (e.g., triclabendazole), levamisole, closantel and development inhibitors such as S-methoprene.

There is a need for a formulation that can be applied as a pour-on or a spot-on formulation but offers higher water resistance and extended duration of efficacy. This will decrease stress to the animals and avoid the labor and costs associated with multiple pour-on applications. It will further avoid labor and costs associated with attaching and retrieving ear tags.

SUMMARY OF THE INVENTION

The topical solution of the invention includes at least one active ingredient and a volatile solvent system that contains at least one dissolved polymer. The solvent system is not designed to maximize spreading, but instead, to have some spreading and to evaporate shortly after dosing, leaving a water-resistant film of polymer on the skin and hair. This could consist of a contiguous film or a conglomerate of polymer particles adhering to hair and skin of an animal. After evaporation of the volatile solvent(s), the active(s), entrapped into the polymer will diffuse out at a specified rate and will be carried by skin lipids of an animal. The active(s) need to be able to dissolve not only in the volatile solvent system, but also in the polymer. The rate of diffusion can be impacted by selection of solvents, their ratios, selection of polymers, addition of a plasticizer(s) and its chemical composition, or by the skin lipids naturally occurring on skin. The selection of excipients also will impact such formulation properties as water resistance, run-off during dosing, and duration of efficacy.

The invention provides for an increased duration of efficacy of a topical formulation through the use of a polymer dissolved in the formulation. As the formulation dries on the surface (either hair or skin), the active ingredient is entrapped in the resulting polymer matrix. The rate of release of the active can be controlled by incorporating and adjusting the amount of a "plasticizer" (i.e., a solvent that is fluid in the solidified polymer). The resultant polymer matrix will then perform similarly to the traditional transdermal patch or ear tag.

In one aspect, the invention is a topical delivery formulation with one or more solvents to include saturated aliphatic ketones, esters and alcohols. The invention further includes a water insoluble polymer alone or in combination with a water soluble polymer, and, optionally a plasticizer.

Examples of solvents include, but are not limited to, methyl isobutyl ketone, butyl acetate, ethyl lactate, isopropyl alcohol or ethanol. Examples of water insoluble polymers include, but are not limited to, vinyl acetate, polyisobutene, methacrylates, polyurethanes, styrenes and polyolefin elastomers. Non-limiting examples of water soluble polymers include povidone, polyvinyl alcohol, polyacrylic acid and ethyl cellulose. The optional plasticizer may be, for example, an aliphatic ester such as acetyl tributyl citrate. Other esters may function as plasticizers, for example, triethyl citrate, tributyl citrate, acetyl triethyl citrate, cetearyl palmitate and lanolin. Further, polymers (e.g., polybutene), oils (e.g., castor oil), and propylene glycol and propylene glycol esters may function as plasticizers. Oily actives, such as pyrethroids (e.g., permethrin) and growth regulators (e.g., (s)-methoprene) can also act as plasticizers.

In another aspect, the invention is a method of making a topical delivery formulation using the solvents, polymers and optional plasticizers described herein.

In yet another aspect, the invention is a use of a topical delivery formulation in the manufacture of a medicament for the therapeutic and/or prophylactic treatment of an animal against an ectoparasite and/or an endoparasite.

DETAILED DESCRIPTION OF THE INVENTION

In one aspect, the invention is a topical delivery formulation with one or more solvents to include saturated aliphatic ketones, esters and alcohols. The invention further includes a water insoluble polymer alone or in combination with a water soluble polymer, and, optionally a plasticizer.

Examples of solvents include, but are not limited to, methyl isobutyl ketone, butyl acetate, ethyl lactate, isopropyl alcohol or ethanol. A non-limiting example of a water insoluble polymer is vinyl acetate. Non-limiting examples of water soluble polymers include povidone, polyvinyl alcohol or ethyl cellulose. The optional plasticizer may be an aliphatic ester such as acetyl tributyl citrate.

Veterinarily active ingredients, which include, but are not limited to, acaricides, anthelmintics, antiparasitics, insecticides and insect repellants, may also be added to the compositions of the invention. Antiparasitic agents can include both ectoparasiticidal and endoparasiticidal agents. These agents are well-known in the art (see e.g. *Plumb' Veterinary Drug Handbook*, 5th Edition, ed. Donald C. Plumb, Blackwell Publishing, (2005) or *The Merck Veterinary Manual*, 9th Edition, (January 2005) and include but are not limited to acarbose, acepromazine maleate, acetaminophen, acetazolamide, acetazolamide sodium, acetic acid, acetohydroxamic acid, acetyl cysteine, acitretin, acyclovir, albendazole, albuterol sulfate, alfentanil HCl, allopurinol, alprazolam, altrenogest, amantadine HCl, amikacin sulfate, aminocaproic acid, aminopentamide hydrogen sulfate, aminophylline/theophylline, amiodarone HCl, amitraz, amitriptyline HCl, amlodipine besylate, ammonium chloride, ammonium molybdenate, amoxicillin, amoxicillin, clavulanate potassium, amphotericin B desoxycholate, amphotericin B lipid-based, ampicillin, amprolium HCl, antacids (oral), antivenin, apomorphione HCl, apramycin sulfate, ascorbic acid, asparaginase, aspiring, atenolol, atipamezole HCl, atracurium besylate, atropine sulfate, aurnofin, aurothioglucose, azaperone, azathioprine, azithromycin, baclofen, barbituates, benazepril HCl, betamethasone, bethanechol chloride, bisacodyl, bismuth subsalicylate, bleomycin sulfate, boldenone undecylenate, bromides, bromocriptine mesylate, budenoside, buprenorphine HCl, buspirone HCl, busulfan, butorphanol tartrate, cabergoline, calcitonin salmon, calcitrol, calcium saits, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur HCl, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine HCl, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol HCl, clindamycin, clofazimine, clomipramine HCl, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine HCl, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine HCl, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin HCl, digoxin, dihydrotachysterol (DHT), diltiazem HCl, dimenhydrinate, dimercaprol/BAL, dimethyl sulfoxide, dinoprost tromethamine, diphenylhydramine HCl, disopyramide phosphate, dobutamine HCl, docusate, dolasetron mesylate, domperidone, dopamine HCl, doramectin, doxapram HCl, doxepin HCl, doxorubicin HCl, doxycycline, edetate calcium disodium, calcium EDTA, edrophonium chloride, enalapril, enoxaparin sodium, enrofloxacin, ephedrine sulfate, epinephrine, epoetin/erythropoietin, eprinomectin, epsiprantel, erythromycin, esmolol HCl, estradiol cypionate, ethacrynic acid/ethacrynate sodium, ethanol (alcohol), etidronate sodium, etodolac, etomidate, euthanasia agents w/pentobarbital, famotidine, fatly acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine HCl, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobln®), heparin, hetastarch, hyaluronate sodium, hydrazaline HCl, hydrochlorothiazide, hydrocodone bitartrate, hydrocortisone, hydromorphone, hydroxyurea, hydroxyzine, ifosfamide, imidacloprid, imidocarb dipropinate, impenem-cilast?ltin sodium, imipramine, inamrinone lactate, insulin, interferon alfa-2a (human recombinant), Iodide (sodium/potassium), ipecac (syrup), ipodate sodium, iron dextran, isoflurane, isoproterenol HCl, isotretinoin, isoxsuprine HCl, itraconazole, ivermectin, kaolin/pectin, ketamine HCl, ketoconazole, ketoprofen, ketorolac tromethamine, lactulose, leuprolide, levamisole, levetiracetam, levothyroxine sodium, lidocaine HCl, lincomycin HCl, liothyronine sodium, lisinoprll, lomustine (CCNU), lufenuron, lysine, magnesium, mannitol, marbofloxacin, mechlorethamine HCl, meclizine HCl, meclofenamic acid, medetomidine HCl, medium chain triglycerides, medroxyprogesterone acetate, megestrol acetate, melarsomine, melatonin, meloxican, melphalan, meperidine HCl, mercaptopurine, meropenem, metformin HCl, methadone HCl, methazolamide, methenamine mandelate/hippurate, methimazole, methionine, methocarbamol, methohexital sodium, methotrexate, methoxyflurane, methylene blue, methylphenidate, methylprednisolone, metoclopramide Hel, metoprolol, metronidaxole, mexiletine HCl, mibolerone, midazolam HCl, milbemycin oxime, mineral oil, minocycline HCl, misoprostol, mitotane, mitoxantrone Hel, morantel tartrate, morphine sulfate, moxidectin, naloxone HCl, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifJoxacin, oxacillin sodium, oxazepam, oxfendazole, oxybutynin chloride, oxymorphone HCl, oxytretracycline, oxytocin, pamidronate disodium, pancreptipase, pancuronium bromide, paromomycin sulfate, parozetine HCl, pencillamine, general information penicillins, penicillin G, penicillin V, potassium, pentazocine, pentobarbital sodium, pentosan polysulfate sodium. pentoxifyiline, pergolide mesylate, phenobarbital, phenoxybenzamine HCl, pheylbutazone, phenylephrine HCl, phenypropanolamine HCl, phenytoin sodium, pheromones, parenteral phosphate, phytonadione/vitamin K-1, pimobendan, piperazine, pirlimycin HCl, piroxicam, polysulfated glycosaminogiycan, ponazuril, potassium chloride, pralidoxime chloride, praziquantel, prazosin HCl, prednisolone/prednisone, primidone, procainamide HCl, procarbazine HCl, prochlorperazlne, propantheline bromide, propofol, propranolol HCl, protamine sulfate, pseudoephedrine HCl, psyllium hydrophilic mucilloid, pyrantel pamoate, pyridostlgmine bromide, pyrilamine maleate, pyrimethamine, quinacrine HCl, quinidine, ranitidine HCl, rifampin, s-adenosyl-methionine (SAMe), saline/hyperosmotic laxative, selamectin, selegiline HCl, deprenyl, sertraline HCl, sevelamer HCl, sevoflurane, silymarin/milk thistle, sodium bicarbonate, sodium polystyrene sulfonate, sodium stibogluconate, sodium sulfate, sodum thiosulfate, somatotropin, sotalol HCl, spectinomycin HCl, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprlm, sulfasalazine, taurine, tepoxaline, terbinafline HCl, terbutaline sulfate, testosterone, tetracycline HCl, thiabendazole, thiacetarsamide sodium, thiamine HCl, thioguanine, thiopental sodium, thyrotropin, tiamulin, ticarcilin disodium, tiletamine HCl, zolazepam HCl, tilmocsin, tiopronin, tobramycin sulfate, tocainide HCl, tolazoline HCl, telfenamic acid, topiramate, tramadol HCl, trimcinolone acetonide, trientine HCl, trilostane, trimepraxine tartrate w/prednisolone, tripelennamine HCl, tylosin, urdosiol, valproic acid, vanadium, vancomycin HCl, vasopressin, vecuronium bromide, verapamil HCl, vinblastine sulfate, vincristine sulfate, vitamin E/selenium, warfarin sodium, xylazine HCl, yohimbine HCl, zidovudine (AZT), zinc acetate/zinc sulfate, zonisamide and mixtures thereof.

In one embodiment of the invention, pyrazole compounds such as phenylpyrazoles, as described above (e.g., fipronil), are known in the art and are suitable actives alone or in combination with other active compounds of the invention. Examples of such pyrazole compounds include but are not limited to those described in U.S. Pat. Nos. 6,001,384; 6,010,710; 6,083,519; 6,096,329; 6,174,540; 6,685,954 6,998,131; 7,759,381 and 8,445,519. Each is assigned to Merial, Ltd., (Duluth, Ga., USA) and incorporated by reference herein. (RS)-5-amino-1-[2,6-dichloro-4-(trifluoromethyl)phenyl]-4-(trifluoromethylsulfinyl)-1H-pyrazole-3-carbonitrile (i.e., fipronil), 1H-pyrazole-3-carbonitrile, 1-[2, 6-dichloro-4-trifluoromethyl)phenyl]-5-methyl-4-[(trifluoromethyl)sulfinyl] (i.e., ML465), and 1-(2-chloro-6-fluoro-4-trifluoromethylphenyl)-4-dichlorofluoro-methylsulfinyl-5-methylpyrazole-3-carbonitrile (i.e., ML198) are specifically referenced.

In another embodiment of the invention, nodulisporic acid and its derivatives (a class of known acaricidal, anthelmintic, anti-parasitic and insecticidal agents) can be added to the compositions of the invention. These compounds are used to treat or prevent infections in humans and animals and are described, for example, in U.S. Pat. Nos. 5,399,582 and 5,962,499. The composition can include one or more of the known nodulisporic acid derivatives in the art, including all stereoisomers, such as those described in the literature cited above.

In another embodiment of the invention, one or more macrocyclic lactones, which act as an acaricide, anthelmintic agent and insecticide, can be added to the compositions of the invention. The macrolides are well-known in the art. See e.g., Macrolides—Chemistry, pharmacology and clinical uses—edited by Bryskier et al., published by Amette Blackwell, (1993). Macrolides include, but are not limited to, 12-membered ring macrolides (e.g. methymycin, neomethymycin, YC-17, litorin); 14-membered ring macrolides (e.g., erythromycin A-F, oleandomycin, sporeamicin, roxithromycin, dirithromycin, flurithromycin, clarithromycin, davercin); 15-membered ring macrolides (e.g., azithromycin); 16-membered ring macrolides (e.g., josamycin, kitasamycin, spiramycin, midecamycin, rokitamycin, miokamicin) and 17-membered ring macrolides (e.g., lankadicin).

The macrocyclic lactones also include, but are not limited to, avermectins, such as abamectin, dimadectin, doramectin, emamectin, eprinomectin, ivermectin, latidectin, lepimectin, selamectin and milbemycins, such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131—each assigned to Merial, Ltd. (Duluth, Ga., USA).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrazik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring; milbemycins lack the glycosidic moiety of the avermectins. The natural product avermectins are disclosed in U.S. Pat. No. 4,310,519 to Albers-Schonberg et al., and the 22,23-dihydro avermectin compounds are disclosed in Chabala et al., U.S. Pat. No. 4,199,569. Mention is also made of Kitano, U.S. Pat. No. 4,468,390, Beuvry et al., U.S. Pat. No. 5,824,653, EP 0 007 812 A1, U.K. Patent Specification 1 390 336, EP 0 002 916, and Ancare New Zealand Patent No. 237 086, inter alia. Naturally occurring milbemycins are described in Aoki et al., U.S. Pat. No. 3,950,360 as well as in the various references cited in "The Merck Index" 12th ed., S. Budavari, Ed., Merck & Co., Inc. Whitehouse Station, N.J. (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. No. 5,077,308, U.S. Pat. No. 4,859,657, U.S. Pat. No. 4,963,582, U.S. Pat. No. 4,855,317, U.S. Pat. No. 4,871,719, U.S. Pat. No. 4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, U.S. Pat. No. 4,920,148 and EP 0 667 054.

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. No. 3,748,356; U.S. Pat. No. 3,818,047; U.S. Pat. No. 4,225,598; U.S. Pat. No. 4,798,837; U.S. Pat. No. 4,751,225, EP 0179022 or U.K. 2 140 010 as well as U.S. Pat. Nos. 6,096,329 and 6,685,954 (both assigned to Merial Ltd., Duluth, Ga.). Examples of IGRs suitable for use include but are not limited to methoprene, pyriproxyfen, hydroprene, cyromazine, fluazuron, lufenuron, novaluron, pyrethroids, formamidines and 1-(2, 6-difluorobenzoyl)-3-(2-fluoro-4-(trifluoromethyl)phenylurea. An anthelmintic agent that can be combined with the compound of the invention to form a composition can be a benzene disulfonamide compound, which includes but is not limited to clorsulon; or a cestodal agent, which includes but is not limited to praziquantel, pyrantel or morantel.

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside.

An insecticidal agent that can be combined with the compound of the invention to form a composition can be a spinosyn (e.g. spinosad) or a substituted pyridylmethyl derivative compound such as imidacloprid. Agents of this class are described above and for example, in U.S. Pat. No. 4,742,060 or in EP 0 892 060. It would be well within the skill level of the practitioner to decide which individual compound can be used in the inventive formulation to treat a particular infestation of an insect.

Insect repellants, alone or in combination with the above, may also be considered actives in the present invention. Examples include pyrethroids such as allethrin, alphamethrin, bioresmethrin, byfenthrin, cycloprothrin, cyfluthirin, decamethrin, cyhalothrin, cypermethrin, deJtamethrin, alpha-cyano-3-phenyl-2-methylbenzyl 2,2-dimethyl-3-(2-chloro-2-trifluoro-methylvinyl)cyclopropane-carboxylate, fenpropathrin, fenfluthrin, fenvalerate, flucythrinate, flumethrin, fluvalinate, permethrin, resmethrin and tralomethrin.

In general, the pesticidal agent or repellant is included in a dose of between about 0.1 μg and about 10 mg. In one embodiment of the invention, the pesticidal agent or repellant is included in a dose of between about 1 μg and about 10 mg. In another embodiment of the invention, the pesticidal agent or repellant is included in a dose of about 5 to about 200 μg/kg of weight of animal. In yet another embodiment of the invention, the pesticidal agent or repellant is included in a dose between about 0.1 to about 10 mg/kg of weight of animal. In still another embodiment of the invention, the pesticidal agent or repellant is included in a dose between about 0.5 to 50 mg/kg.

The proportions, by weight, of the 1-aryl-5-alkyl pyrazole compound and any additional pesticidal agent are, for example, between about 5/1 and about 10,000/1. However, one of ordinary skill in the art would be able to select the appropriate ratio of 1-aryl-5-alkyl pyrazole compound and the additional pesticidal agent for the intended host and use thereof.

In another embodiment of the invention, the formulation can be in ready-to-use solution form as is described in U.S. Pat. No. 6,395,765, incorporated herein by reference. In addition to the active(s) compound, the solution can contain a crystallization inhibitor. The crystallization inhibitor can be present in a proportion of about 1 to about 20% (w/v). Alternatively, the crystallization inhibitor can be present in a proportion of about 5 to about 15%. In another embodiment of the amount of crystallization inhibitor, the amount corresponds to the test in which 0.3 ml of a solution comprising 10% (w/v) of 1-aryl-5-alkyl pyrazole compound in the liquid carrier and 10% of the inhibitor are deposited on a glass slide at 20° C. and allowed to stand for 24 hours. The slide is then observed with the naked eye. Acceptable inhibitors are those whose addition provides for few (e.g., less than ten crystals) or no crystal.

Crystallization inhibitors which are useful for the invention include but are not limited to:

(a) polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates;

(b) anionic surfactants, such as alkaline stearates (e.g., sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g., coconut oil);

(c) cationic surfactants, such as water-soluble quaternary ammonium salts of formula N+R'R''R'''R''''Y−, in which the R radicals are identical or different optionally hydroxylated hydrocarbon radicals and Y− is an anion of a strong acid, such as halide, sulphate and sulphonate anions; cetyltrimethylammonium bromide is one of the cationic surfactants which can be used;

(d) amine salts of formula N+R'R''R''', in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g., Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In another embodiment of the invention, the formulation can also comprise an antioxidizing agent intended to inhibit oxidation in air. This agent may be present in a proportion of about 0.005 to about 1% (w/v) Alternatively, the antioxidizing agent may be present in a proportion of about 0.01 to about 0.05%. Antioxidizing agents include, but are not limited to, butylated hydroxyanisole, butylated hydroxy toluene, ascorbic acid, sodium metabisulphite, propyl gallate, sodium thiosulphate or a mixture of not more than two of the above.

Embodiments of the invention may also include colorants, fragrances and pH stabilizers known in the art. Examples of colorants include, but are not limited to, titanium dioxide and iron oxide. A comprehensive list of acceptable colorants may be found at 37 CFR, Title 21, Part 74. Colorants and pH stabilizers are conventional and known in the art.

The invention is also directed toward a method of treating an animal (e.g., a mammal), against ectoparasitic infection by administering an ectoparasiticidally effective amount of the composition of the invention. Mammals which can be treated include, but are not limited to, humans, cats, dogs, cattle, chickens, cows, deer, goats, horses, llamas, pigs, sheep and yaks. In one embodiment of the invention, the mammals treated are humans, cats or dogs.

In another embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma. Damalinia, Linognathus, Haematopinus, Solenoptes, Trichodectes,* and *Felicola.*

In another embodiment for the treatment against ectoparasites, the ectoparasite is from the genera *Ctenocephalides, Rhipicephalus, Dermacentor, Ixodes* and/or *Boophilus.* The ectoparasites treated include but are not limited to fleas, ticks, mites mosquitoes, flies, lice, blowfly and combinations thereof. Specific examples include but are not limited to cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dematobia* sp., *Cochliomyia* sp., and the like). In yet another embodiment for the treatment against ectoparasites, the ectoparasite is a flea and/or tick.

Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the paraSite, such as *Haematobia irritans* (horn fly): lice such as *Linognathus vitulorum*, etc.; and mites such as *Sarcoptes scabici* and *Psoroptes ovis*. The above list is not exhaustive and other ectoparasites are well known in the art to be harmful to animals and humans. These include, for example migrating dipterous larvae.

When an anthelmintic agent is added to the composition of the invention, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, FaSCiola, Haemonchus, Oesophagostumum, Osteriagia, Toxocara, Strongyloides, Toxascaris, Trichinella, Trichuris*, and *Trichostrongylus*.

In another embodiment, the compounds of the invention are administered in spot-on formulations. While not wishing to be bound by theory, it is believed that these formulations work by gradual diffusion of active(s) encapsulated into the polymer or blend of polymers that adhere to hair and skin after evaporation of solvent(s), and dissolution of the dose in the natural oils of the host's skin or fur. Thus, the polymer becomes is a reservoir that stores and protects active(s) from environmental stress, such as rain, for the duration of the treatment period, and active(s) continues to gradually diffuse from the polymer and replenish the therapeutic amounts of active(s) washed off during rain or removed by other means (e.g., licking, rubbing). From there, the active agent(s) distribute around the host's body through the sebaceous glands of the skin. The therapeutic agent also remains in the sebaceous glands.

In one embodiment of the location of administration, a single formulation containing the active agent in a substantially liquid carrier and in a form which makes possible a single application, (e.g., as a pour-on or can be applied as a spot-on at one or multiple locations of the animal's body) will be administered to the animal over a localized region of the animal, e.g., between the two shoulders or along the spine. The invention is further described by the following non-limiting examples which further illustrate the invention, and are not intended, nor should they be interpreted to, limit the scope of the invention.

In one application of the invention, *Haematobia irritans* (L., i.e., horn fly), is a pest of cattle that causes significant economic losses estimated at more than $1 billion in the United States annually. Horn fly infestation leads to decreased milk production, decreased weaning weights of calves, and decreased weight gains on growing cattle. (Domingues, L. N., et al., Discovery of the Rdl mutation in association with a cyclodiene resistant population of horn flies, *Haematobia irritans* (Diptera: Musidae). Vet. Parasitol. (2013)).

Current commercially available topical solutions to control horn fly population on cows provide limited duration of protection lasting from several days to about two weeks. Current treatments further require frequent re-application due to a wash-off after exposure to environmental conditions such as rain. Extension of efficacy to one month or longer will provide continuous protection against the horn fly with less frequent applications. Fewer applications will be less stressful for the animals and less time and labor consuming for the farmers. This may be accomplished by using active ingredients of superior efficacy, by using an enhanced delivery mechanism, or both.

Although many different actives may work with the formulation of the invention, 1H-pyrazole-3-carbonitrile, 1-[2,6-dichloro-4-(trifluoromethyl)phenyl]-5-methyl-4-[(trifluoromethyl)sulfinyl] (i.e., ML465) is the compound used to test topical formulations for control of horn fly on cows for a duration of one month or longer.

Water Resistance

In-vivo and in-vitro studies were conducted to compare wash-off resistance of formulations prepared with lipophilic solvents and with polymers. Results indicate that a wash-off resistance is higher for formulations with polymers. Water resistance of known solvent systems used in clinical in-vivo studies A and B was evaluated and results are summarized in Table 1 Table 1 below shows water resistance of conventional pour-on formulations used in clinical studies A and B.

TABLE 1

| in-vivo Efficacy study | % ML465 in Solutions, w/v | Solvent System | Duration of above 90% efficacy (days) |
|---|---|---|---|
| A | 3.0 | 30% Tributyl acetyl citrate Miglyol 840 | 17 |
| B | 0.5 | 30% Tributyl acetyl citrate 5% Polypropylene Glycol (15) stearyl ether Soybean Oil | 17 |
| B | 1.0 | 30% Tributyl acetyl citrate 3% Polypropylene Glycol (15) stearyl ether 8.5% Isopropyl palmitate 7% Isobutene H25 Soybean Oil | 17 |
| B | 1.0 | 30% Tributyl acetyl citrate 3% Polypropylene Glycol (15) stearyl ether 10% Isopropyl palmitate 7% cetearyl octanoate 10% butyl stearate Soybean Oil | 24 |

Trials A and B with traditional formulations containing ML465 did not result in a desired duration of efficacy due to the impact of water exposure during rains which occur randomly and have highly variable intensity. It can be seen that the amount of ML465 washed off is at, or below, 10% of the applied dose, indicating a sharp decrease upon exposure to water. This was not sufficient to support thirty days efficacy duration. Thus, efficacy may depend on resistance of the solvent system to water exposure.

The in-vivo studies of Table 1 were followed with in-vitro studies conducted to assess water resistance of "conventional" solvent systems. Conventional pour-on solvent formulations described below were tested using ML465 as the active under exposure to water for 20 and 40 minutes.

TABLE 2

| | In-lab Water Resistance (% ML465 Removed after Water Exposure (n = 2)) | |
|---|---|---|
| Description of Solvent System | 20 min | 40 min |
| 30% Tributyl acetyl citrate Miglyol 840 | 2.4% | 5.2% |
| 30% Tributyl acetyl citrate 5% PPG-15 stearyl ether Soybean oil | 7.5% | 10.1% |
| 30% Tributyl acetyl citrate 5% PPG-15 stearyl ether 6% Isobutene H25 Soybean Oil | 5.2% | 7.3% |
| 30% Tributyl acetyl citrate 5% PPG-15 stearyl ether 10% Isopropyl palmitate 10% ceteary octanote 10% butyl stearate Soybean Oil | 8.8% | 9.2% |

Laboratory data indicate that ML465 is washed off after repeated exposure to water for all formulations tested. It means that with each rainfall, of random duration and intensity, the concentration of ML465 on the skin will gradually decrease.

Next, the water resistance of the inventive solvent systems was tested in vitro. Table 3 shows the percentage of ML465 active lost upon exposure to water for 40 minutes. The formulation of the invention lowered (i.e., improved) the percentage of ML465 removed after exposure to water compared with the conventional solvent systems in Tables 1 and 2.

TABLE 3

| Sample ID | Solvent systems with 1% w/w ML465 | In-lab Water Resistance (% ML 465 Removed after 40 min. water exposure (n = 2)) |
|---|---|---|
| 36 | Methyl isobutyl ketone + 10% Polyvinyl Acetate + Isopropanol | 2.3% |

The entrapment of an active into the polymer and continuous diffusion of an active out of the polymer will ensure protection from environmental conditions such as rain, and continuous replenishment and presence of an active on skin to provide treatment for the duration of the desired treatment period. Lipids present on animal skin will act as a carrier and will also be continuously replenished by the animal.

The rate of diffusion can be controlled through the composition of the polymer part of the formulation, such as use of a single polymer, blends of various polymers, or polymers of various molecular weights. Furthermore, the rate of diffusion can also be controlled by addition of a plasticizer in varying compositions and amounts. The plasticizer can be an external agent or the sebacious lipids naturally present on the skin.

This formulation for topical delivery of a pharmaceutical active ingredient is through the application of a liquid formulation with a solvent system consisting of a single volatile solvent or a combination of volatile solvents, a polymer or a combination of polymers, one or several actives, and optionally a plasticiser or a combination of plasticisers. The examples of solvent systems tested are presented below. It should be possible for one skilled in the art to create additional examples that would broaden the classes of materials that could be utilized. Solvents envisioned by the present invention include a saturated aliphatic ketone (e.g., methyl isobutyl ketone) or an ester (e.g., butyl acetate or ethyl lactate). These solvents could further be combined with, for example, isopropyl alcohol or ethanol. Polymers envisioned by the present invention include at least a water insoluble polymer (e.g., a polyvinyl acetate of varying molecular weights) that may be combined with water soluble polymers (e.g., povidones, polyvinyl alcohol or ethyl cellulose).

Optionally, the formulation of the present invention may include an external aliphatic ester plasticizer (e.g., acetyl tributyl citrate), fragrances and coloring agents.

It should be noted that isopropanol may be a solvent or a plasticizer. Neither polymer nor ML465 dissolve in isopropanol. It was added initially to reduce the strong odor of methyl isobutyl ketone. Surprisingly, it was observed that addition of isopropanol impacts the rate of release of ML465 from the matrix, thus making isopropanol a plasticizer in this case. For other actives that either can be miscible with or dissolve in isopropanol, it can be a solvent.

After dosing, the liquid formulation does not have to spread to cover a body of an animal like a conventional topical formulation. A volatile solvent(s) evaporates faster, leaving a polymer matrix patch that may not be evenly distributed around an application spot. The polymer will adhere to hair or skin carrying an active that is entrapped in the polymer. The theraputic effect is achieved by diffusion of the active(s) out of the polymer and blending with the lipids present on an animal's skin that will carry it to cover the animal's body. The degree of spreading of the formulation can be controlled through the selection of solvents and spreading agents. Surprisingly, the addition of isopropanol to methyl isobutyl ketone during solution preparation resulted in an equal or even greater rate of API diffusion out of the API/polymer mixture compared to API/polymer mixture with addition of a plasticizer Isopropanol is not considered to be a traditional plasticizer for the polymer. It is postulated that its effect may be on the physical structure of the polymer film (such as creating additional porosity). The concentration of isopropanol can be below, equal or greater than concentration of polymer, with the upper limit being a solubility of polymer/polymer combination in a solvent system. Polyvinyl acetate does not dissolve in isopropanol, therefore isopropanol cannot replace methyl isobutyl ketone completely as there should be a sufficient amount of methyl isobutyl ketone for polymer to dissolve.

This approach can be utilized to topically deliver various actives to production animals such as cows, sheep, swine, horses, or companion animals, such as dogs and cats, and others to protect against external parasites (e.g., fleas, ticks, mites, flies, etc.) or internal parasites.

Several embodiments of the invention are given in the following examples.

EXAMPLE 1

| Ingredients | Function | % w/w |
|---|---|---|
| ML465 | Active | 4.0 |
| Polyvinyl acetate MW 100000 | Polymer | 14.4 |
| methyl isobutyl ketone | Solvent | QS to 100% |

Process: add methyl isobutyl ketone, in the amount of about 40% of the weight to be prepared, into the container that can be tightly closed during preparation of formulation; add polymer and mix until it dissolves, about 2-3 hours; add ML465, mix until dissolved; QS 100% with methyl isobutyl ketone, mix. Make sure the container is tightly closed to prevent evaporation of solvent.

EXAMPLE 2

| Ingredients | Function | % w/w |
|---|---|---|
| ML465 | Active | 4.0 |
| Polyvinyl acetate MW 100000 | Polymer | 7.2 |
| Polyvinyl acetate MW 50000 | Polymer | 7.2 |
| methyl isobutyl ketone | Solvent | QS to 100% |

Process: add methyl isobutyl ketone, in the amount of about 40% of the weight to be prepared, into the container that can be tightly closed during preparation of formulation; add polymers and mix until it dissolves, about 23 hours; add ML465, mix until dissolved; QS 100% with methyl isobutyl ketone, mix. Make sure the container is tightly closed to prevent evaporation of solvent.

EXAMPLE 3

| Ingredients | Function | % w/w |
|---|---|---|
| ML465 | Active | 4.0 |
| Polyvinyl acetate MW 100000 | Polymer | 14.4 |
| Isopropanol | Additive | 25.0 |
| methyl isobutyl ketone | Solvent | QS to 100% |

Process: add methyl isobutyl ketone, in the amount of about 40% of the weight to be prepared, into the container that can be tightly closed during preparation of formulation; add polymer and mix until it dissolves, about 2-3 hours; add ML465, mix until dissolved; slowly add isopropanol—whilte flakes will be formed, continue to mix until flakes dissolve and solution is clear, can add remaining methyl isopropyl ketone and mix until solution is clear. Make sure the container is tightly closed to prevent evaporation of solvent.

EXAMPLE 4

| Ingredients | Function | % w/w |
|---|---|---|
| ML465 | Active | 4.0 |
| Polyvinyl acetate MW 100000 | Polymer | 20.0 |
| methyl isobutyl ketone | Solvent | QS to 100% |

Process: add methyl isobutyl ketone, in the amount of about 55% of the weight to be prepared, into the container that can be tightly closed during preparation of formulation; add polymer and mix until it dissolves, about 2-3 hours; add ML465, mix until dissolved; QS 100% with methyl isobutyl ketone, mix. Make sure the container is tightly closed to prevent evaporation of solvent.

EXAMPLE 5

| Ingredients | Function | % w/w |
|---|---|---|
| ML465 | Active | 4.0 |
| Polyvinyl acetate MW 100000 | Polymer | 20.0 |
| Isopropanol | Additive | 8.5 |
| methyl isobutyl ketone | Solvent | QS to 100% |

Process: add methyl isobutyl ketone, in the amount of about 55% of the weight to be prepared, into the container that can be tightly closed during preparation of formulation; add polymer and mix until it dissolves, about 2-3 hours; add ML465, mix until dissolved; slowly add isopropanol—whilte flakes will be formed, continue to mix until flakes dissolve and solution is clear, can add remaining methyl isopropyl ketone at the same time as isopropanol and mix until solution is clear. Make sure the container is tightly closed to prevent evaporation of solvent.

EXAMPLE 6

| Ingredients | Function | % w/w |
|---|---|---|
| ML465 | Active | 4.0 |
| Polyvinyl acetate MW 100000 | Polymer | 20.0 |
| Isopropanol | Additive | 8.5 |
| Acetyl tributyl citrate | Plasticizer | 2.0 |
| methyl isobutyl ketone | Solvent | QS to 100% |

Process: add methyl isobutyl ketone, in the amount of about 55% of the weight to be prepared, into the container that can be tightly closed during preparation of formulation; add polymer and mix until it dissolves, about 2-3 hours; add ML465, mix until dissolved; add acetyl tributyl citrate; slowly add isopropanol—whilte flakes will be formed, the remaining methyl isopropyl ketone can be added at the same time as addition of isopropanol, continue to mix until flakes dissolve and solution is clear, can add remaining methyl isopropyl ketone at the time of and mix until solution is clear. Make sure the container is tightly closed to prevent evaporation of solvent.

EXAMPLE 7

| Ingredients | Function | % w/w |
|---|---|---|
| ML465 | Active | 4.0 |
| Polyvinyl acetate MW 100000 | Polymer | 20.0 |
| Isopropanol | Additive | 25 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add ML465, mix until dissolved; slowly add isopropanol—white flakes will be formed, continue to mix until flakes dissolve and solution is clear, the remaining methyl isopropyl ketone can be added at the same time as addition of isopropanol, and mix until solution is clear. Make sure the container is tightly closed to prevent evaporation of solvent.

EXAMPLE 8

| Ingredients | Function | % w/w |
|---|---|---|
| ML465 | Active | 4.0 |
| Polyvinyl acetate MW 100000 | Polymer | 14.0 |
| Acetyl tributyl citrate | Plasticizer | 3.0 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add ML465, mix until dissolved; add acetyl tributyl citrate and the remaining methyl isopropyl ketone and mix. Make sure the container is tightly closed to prevent evaporation of solvent.

EXAMPLE 9

| Ingredients | Function | % w/w |
|---|---|---|
| Permethrin | Active | 10.0 |
| Polyvinyl acetate MW 100000 | Polymer | 20.0 |
| methyl isobutyl ketone | Solvent | QS to 100% |

Process: add methyl isobutyl ketone, in the amount of about 65% of the weight to be prepared, into the container that can be tightly closed during preparation of formulation; add polymer and mix until it dissolves, about 2-3 hours; add permethrin and mix; QS 100% with methyl isobutyl ketone, mix. Make sure the container is tightly closed to prevent evaporation of solvent.

EXAMPLE 10

| Ingredients | Function | % w/w |
|---|---|---|
| Permethrin | Active | 10.0 |
| Polyvinyl acetate MW 100000 | Polymer | 20.0 |
| Isopropanol | Additive | 15.0 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add permethrin, mix; slowly add isopropanol—white flakes will be formed, continue to mix until flakes dissolve and solution is clear, the remaining methyl isopropyl ketone can be added at the same time as addition of isopropanol, and mix until solution is clear. Make sure the container is tightly closed to prevent evaporation of solvent.

EXAMPLE 11

| Ingredients | Function | % w/w |
|---|---|---|
| Permethrin | Active | 10.0 |
| Polyvinyl acetate MW 100000 | Polymer | 15.0 |
| Isopropanol | Additive | 20.0 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add permethrin, mix; slowly add isopropanol—white flakes will be formed, continue to mix until flakes dissolve and solution is clear, the remaining methyl isopropyl ketone can be added at the same time as addition of isopropanol, and mix until solution is clear. Make sure the container is tightly closed to prevent evaporation of solvent.

EXAMPLE 12

| Ingredients | Function | % w/w |
|---|---|---|
| Permethrin | Active | 10.0 |
| Polyvinyl acetate MW 100000 | Polymer | 20.0 |
| Tributyl acetyl citrate | Plasticizer | 3.0 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add permethrin, mix; add tributyl acetyl citrate and the remaining methyl isopropyl ketone and mix. Make sure the container is tightly closed to prevent evaporation of solvent.

EXAMPLE 13

| Ingredients | Function | % w/w |
|---|---|---|
| Permethrin | Active | 10.0 |
| Polyvinyl acetate MW 100000 | Polymer | 20.0 |
| Tributyl acetyl citrate | Plasticizer | 1.5 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add permethrin, mix; add tributyl acetyl citrate and the remaining methyl isopropyl ketone and mix. Make sure the container is tightly closed to prevent evaporation of solvent.

EXAMPLE 14 [DID NOT PREPARE WITH ACTIVE, BUT PREPARED WITHOUT ACTIVE]

| Ingredients | Function | % w/w |
|---|---|---|
| ML465 | Active | 4.0 |
| Polyvinyl acetate MW 100000 | Polymer | 43.0 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add ML465, mix until dissolved; add the remaining methyl isopropyl ketone and mix. Make sure the container is tightly closed to prevent evaporation of solvent.

EXAMPLE 15

| Ingredients | Function | % w/w |
|---|---|---|
| ML465 | Active | 4.0 |
| Polyvinyl acetate MW 50000 | Polymer | 15.0 |
| Acetyl tributyl citrate | Plasticizer | 3.0 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add ML465, mix until dissolved; add acetyl tributyl citrate and the remaining methyl isopropyl ketone and mix. Make sure the container is tightly closed to prevent evaporation of solvent.

EXAMPLE 16 (DID NOT PREPARED EXACTLY WITH PVAC MW 50000, BUT PREPARED WITH MW 100000)

| Ingredients | Function | % w/w |
|---|---|---|
| ML465 | Active | 4.0 |
| Polyvinyl acetate MW 50000 | Polymer | 15.0 |
| Acetyl tributyl citrate | Plasticizer | 3.0 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add ML465, mix until dissolved; add acetyl tributyl citrate and the remaining methyl isopropyl ketone and mix. Make sure the container is tightly closed to prevent evaporation of solvent.

EXAMPLE 17

| Ingredients | Function | % w/w |
|---|---|---|
| ML465 | Active | 4.0 |
| Polyvinyl acetate MW 50000 | Polymer | 15.0 |
| Isopropanol | Additive | 25.0 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add ML465, mix until dissolved; slowly add isopropanol—white flakes will be formed, continue to mix until flakes dissolve and solution is clear, the remaining methyl isopropyl ketone can be added at the same time as addition of isopropanol, mix until solution is clear. Make sure the container is tightly closed to prevent evaporation of solvent.

EXAMPLE 18

| Ingredients | Function | % w/w |
|---|---|---|
| ML465 | Active | 4.0 |
| Polyvinyl acetate MW 50000 | Polymer | 7.2 |
| Polyvinyl acetate MW 100000 | Polymer | 7.2 |
| Isopropanol | Additive | 25.0 |
| methyl isobutyl ketone | Solvent | QS to 100% |

Process: add methyl isobutyl ketone, in the amount of about 50% of the weight to be prepared, into the container that can be tightly closed during preparation of formulation; add polymers and mix until it dissolves, about 2-3 hours; add ML465, mix until dissolved; slowly add isopropanol—white flakes will be formed, continue to mix until flakes dissolve and solution is clear, the remaining methyl isopropyl ketone can be added at the same time as addition of isopropanol, mix until solution is clear. Make sure the container is tightly closed to prevent evaporation of solvent.

EXAMPLE 19

| Ingredients | Function | % w/w |
|---|---|---|
| ML465 | Active | 4.0 |
| Polyvinyl acetate MW 100000 | Polymer | 13.0 |
| Kollidon SR | Polymer | 1.4 |
| Isopropanol | Additive | 25.0 |
| methyl isobutyl ketone | Solvent | QS to 100% |

Process: add methyl isobutyl ketone, in the amount of about 50% of the weight to be prepared, into the container that can be tightly closed during preparation of formulation; add polyvinyl acetate MW 100000 and mix until it dissolves, about 2-3 hours; add ML465, mix until dissolved; slowly add isopropanol—white flakes will be formed, continue to mix until flakes dissolve and solution is clear; add Kollidon SR and mix until dissolved; the remaining methyl isopropyl ketone can be added at the same time as addition of Kollidon SR, mix until solution is clear. Make sure the container is tightly closed to prevent evaporation of solvent.

EXAMPLE 20 FILM MADE FROM THIS SOLUTION CRYSTALLIZED

| Ingredients | Function | % w/w |
|---|---|---|
| ML465 | Active | 4.0 |
| Polyvinyl acetate MW 100000 | Polymer | 20.0 |
| Isopropanol | Additive | 8.0 |
| Acetyl tributyl citrate | Plasticizer | 12.5 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add ML465, mix until dissolved; add acetyl tributyl citrate and mix; slowly add isopropanol—white flakes will be formed, continue to mix until flakes dissolve and solution is clear; the remaining methyl isopropyl ketone can be added at the same time as addition of isopropanol. Make sure the container is tightly closed to prevent evaporation of solvent.

EXAMPLE 21 FILM MADE FROM THIS SOLUTION CRYSTALLIZED

| Ingredients | Function | % w/w |
|---|---|---|
| ML465 | Active | 4.0 |
| Polyvinyl acetate MW 100000 | Polymer | 14.4 |
| Isopropanol | Additive | 22.0 |
| Acetyl tributyl citrate | Plasticizer | 5.0 |
| methyl isobutyl ketone | Solvent | QS to 100% |

Process: add methyl isobutyl ketone, in the amount of about 50% of the weight to be prepared, into the container that can be tightly closed during preparation of formulation; add polymer and mix until it dissolves, about 2-3 hours; add ML465, mix until dissolved; add acetyl tributyl citrate and mix; slowly add isopropanol—white flakes will be formed, continue to mix until flakes dissolve and solution is clear; the remaining methyl isopropyl ketone can be added at the same time as addition of isopropanol. Make sure the container is tightly closed to prevent evaporation of solvent.

What is claimed is:

1. A topical delivery formulation in the form of a solution, which comprises:
   at least one veterinary active ingredient having ectoparasiticidal activity;
   a volatile solvent system containing at least one dissolved polymer,
      wherein said volatile solvent system comprises one or more solvent(s) selected from the group consisting of saturated aliphatic ketones, esters and alcohols, and wherein the volatile solvent represents from about 50 to about 94% w/w of the composition;
      wherein said polymer comprises a water insoluble polymer that is polyvinyl acetate, alone or in combination with a water soluble polymer; and
   optionally a plasticizer;
wherein after dosing, evaporation of the volatile solvent system provides a water resistant polymer matrix in which the veterinary active ingredient is entrapped.

2. The formulation of claim 1, wherein the solvent is methyl isobutyl ketone.

3. The formulation of claim 1, wherein the solvent is butyl acetate.

4. The formulation of claim 1, wherein the solvent is ethyl lactate.

5. The formulation of claim 1, wherein the polyvinyl acetate is polyvinyl acetate MW 100,000.

6. The formulation of claim 1, wherein the polyvinyl acetate is polyvinyl acetate MW 50,000.

7. The formulation of claim 1, wherein the water soluble polymer is a povidone.

8. The formulation of claim 1, wherein the water soluble polymer is polyvinyl alcohol.

9. The formulation of claim 1, wherein the water soluble polymer is ethyl cellulose.

10. The formulation of claim 1, wherein the optional plasticizer is an aliphatic ester.

11. The formulation of claim 10, wherein the aliphatic ester is acetyl tributyl citrate.

12. The formulation of claim 1, wherein the water insoluble polymer is from about 5% to about 40% w/w of the composition.

13. The formulation of claim 1, wherein the water soluble polymer is from about 5% to about 40% w/w of the composition.

14. The composition of claim 1, wherein the plasticizer is from about 0.5% to about 5% w/w of the composition.

15. A method for the therapeutic and/or prophylactic treatment of an animal against ectoparasitic infections of said animal comprising administering to the animal a topical delivery formulation according to claim 1.

* * * * *